(12) United States Patent
Iizuka et al.

(10) Patent No.: US 10,741,277 B2
(45) Date of Patent: Aug. 11, 2020

(54) INFORMATION PROCESSING APPARATUS, METHOD, SYSTEM, AND STORAGE MEDIUM FOR IMAGE DISPLAY

(71) Applicant: CANON KABUSHIKI KAISHA, Tokyo (JP)

(72) Inventors: Yoshio Iizuka, Takatsuki (JP); Yukari Nakashoji, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 184 days.

(21) Appl. No.: 15/940,726

(22) Filed: Mar. 29, 2018

(65) Prior Publication Data

US 2018/0301215 A1    Oct. 18, 2018

(30) Foreign Application Priority Data

Apr. 13, 2017  (JP) ................................ 2017-079435

(51) Int. Cl.
| | |
|---|---|
| G16H 30/40 | (2018.01) |
| G06T 7/00 | (2017.01) |
| G06F 3/0485 | (2013.01) |
| A61B 5/00 | (2006.01) |
| G16H 40/63 | (2018.01) |
| G06F 3/0484 | (2013.01) |
| G16H 30/20 | (2018.01) |
| A61B 6/00 | (2006.01) |
| A61B 5/055 | (2006.01) |

(52) U.S. Cl.
CPC .......... *G16H 30/40* (2018.01); *A61B 5/7425* (2013.01); *G06F 3/0484* (2013.01); *G06F 3/0485* (2013.01); *G06T 7/0012* (2013.01); *G16H 30/20* (2018.01); *G16H 40/63* (2018.01); *A61B 5/055* (2013.01); *A61B 6/461* (2013.01); *G06T 2207/10072* (2013.01)

(58) Field of Classification Search
None
See application file for complete search history.

(56) References Cited

U.S. PATENT DOCUMENTS

| | | | |
|---|---|---|---|
| 2007/0071297 A1* | 3/2007 | Geiger | A61B 5/4255 382/128 |
| 2008/0175459 A1* | 7/2008 | Geiger | A61B 5/4255 382/131 |
| 2009/0080744 A1* | 3/2009 | Sagawa | G06F 19/321 382/131 |
| 2014/0039318 A1* | 2/2014 | Zhang | G06T 7/0012 600/443 |

* cited by examiner

*Primary Examiner* — Tahmina N Ansari
(74) *Attorney, Agent, or Firm* — Canon U.S.A., Inc. IP Division

(57) ABSTRACT

An information processing apparatus acquires, for each of a plurality of three-dimensional images, information about a position where a two-dimensional image included in the three-dimensional image is present, identifies, based on an instruction about a position of a two-dimensional image to be displayed at a display unit, a three-dimensional image to be a target of the instruction, and identifies, based on information about the position specified by the instruction, and the information about the position where the two-dimensional image is present for each of the plurality of three-dimensional images, a two-dimensional image which is included in the identified three-dimensional image, and which is to be displayed at the display unit.

11 Claims, 6 Drawing Sheets

INFORMATION PROCESSING APPARATUS, METHOD, SYSTEM, AND STORAGE MEDIUM FOR IMAGE DISPLAY

BACKGROUND

Field of the Disclosure

The present disclosure generally relates to information processing and, more particularly, to an information processing apparatus, an information processing method, an information processing system, and a storage medium.

Description of the Related Art

When a doctor performs a diagnosis, the doctor may observe a plurality of medical images while comparing the plurality of medical images, for discovery of a lesion part or follow-up. U.S. Patent Application Publication No. 2009/0080744 A1 to Sagawa discusses a related technique. According to the Sagawa technique, a correspondence relation is obtained by calculating an imaging position of each of a current image and a past image. For example, in a case where a sliced image of the current image is displayed, the display is switched to the corresponding sliced image of the past image, based on the correspondence relation. In other words, the sliced image of the current image and the sliced image of the past image are scrolled in an interlocking manner.

SUMMARY

According to one or more aspects of the present disclosure, an information processing apparatus includes an acquiring unit configured to acquire, for each of a plurality of three-dimensional images, information about a position where a two-dimensional image included in the three-dimensional image is present, a first identification unit configured to identify, based on an instruction about a position of a two-dimensional image to be displayed at a display unit, a three-dimensional image to be a target of the instruction, and a second identification unit configured to identify, based on information about the position specified by the instruction, and the information about the position where the two-dimensional image is present for each of the plurality of three-dimensional images, a two-dimensional image which is included in the identified three-dimensional image, and which is to be displayed at the display unit.

Further features of the present disclosure will become apparent from the following description of exemplary embodiments with reference to the attached drawings.

DESCRIPTION OF THE EMBODIMENTS

Exemplary embodiments of the present disclosure will be described below with reference to the drawings.

A first exemplary embodiment will be described. In the medical field, image diagnosis is performed. For example, a diagnosis is performed based on a medical image obtained by an imaging apparatus such as an X-ray computer tomography (CT) apparatus or a magnetic resonance imaging (MRI) apparatus. A doctor performing an image diagnosis identifies a lesion visualized in a medical image or a symptom of a patient who is an object, by making an overall determination from a finding and various measurement values obtained from the image. In the image diagnosis, there is a case where a comparison is made between a plurality of medical images obtained by different imaging apparatuses, or between a plurality of medical images captured at different times.

In a case where medical images are compared, these images are scrolled while being interlocked with each other. In this case, there is a possibility that an image may be overlooked if sliced images are not scrolled at an appropriate interval. The information processing apparatus according to the first exemplary embodiment allows easy operation for comparing a plurality of medical images, and provides improvement over the art.

Figure 1:
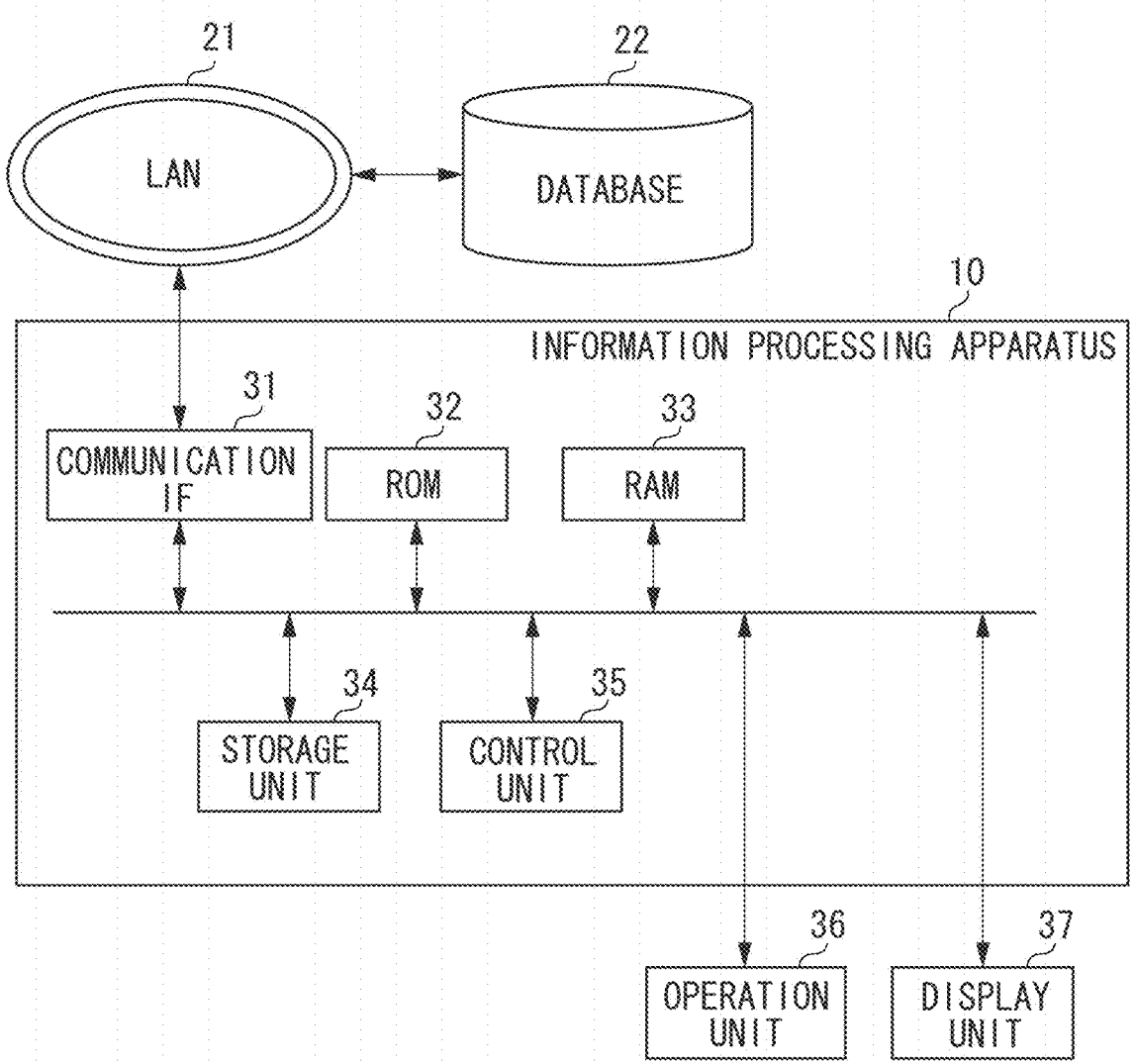
FIG. 1 illustrates an example of a configuration of a system including an information processing apparatus according to an exemplary embodiment of the present disclosure.

FIG. 1 illustrates an example of a configuration of a system including an information processing apparatus 10. The information processing apparatus 10 is connected to a database 22, via a way of communication such as a local area network (LAN) 21.

The database 22 stores a medical image and various data related to the medical image. The database 22 is, for example, a picture archiving and communication system (PACS). The information processing apparatus 10 acquires data such as a medical image from the database 22 via the LAN 21.

The information processing apparatus 10, for example, may be a computer, computerized configuration(s), or the like. The information processing apparatus 10 includes a communication interface (IF) 31, a read only memory (ROM) 32, a random access memory (RAM) 33, a storage unit 34, and a control unit 35.

The communication IF 31 is configured of, for example, a LAN card. The communication IF 31 performs communication between the information processing apparatus 10 and an external apparatus such as the database 22. The communication IF 31 stores, for example, to-be-output information into a transfer packet, and outputs the information to an external apparatus via the LAN 21, by using a communication technology such as Transmission Control Protocol/Internet Protocol (TCP/IP). The information processing apparatus 10 may have a plurality of communication IFs according to a desired communication form.

The ROM 32 is configured of a component such as a nonvolatile memory. The ROM 32 stores a program and data about a procedure of control by the control unit 35. The ROM 32 stores a boot program and various initial data of the information processing apparatus 10. The ROM 32 also stores various programs for implementing processing of the information processing apparatus 10.

The RAM 33 is configured of a component such as a volatile memory. When the control unit 35 performs control based on a command program, the RAM 33 provides a storage area for work. The RAM 33 temporarily stores a program for executing processing in the information processing apparatus 10 and each unit connected thereto, and information such as various parameters to be used for information processing.

The storage unit 34 may be configured of, for example, a hard disk drive (HDD) or a solid state drive (SSD). The storage unit 34 stores information based on control from each configuration connected to the storage unit 34.

The control unit 35 may be configured of, for example, a central processing unit (CPU), a graphics processing unit (GPU), or the like. The control unit 35, which may include one or more processors and one or more memories, may comprehensively control the information processing apparatus 10 and each unit connected to thereto. The control unit 35 performs control by executing a program stored in the ROM 32. Further, the control unit 35 performs input/output control for an operation unit 36. Furthermore, the control unit 35 executes a display driver, which is a piece of software for controlling a display unit 37, and thereby performs display control for the display unit 37.

The CPU and the GPU, which are examples of the configuration of the control unit 35, are included in examples of a processor. Further, the ROM 32, the RAM 33, and the storage unit 34 are included in examples of a memory. The information processing apparatus 10 may have one or more processors and one or more memories. In the first exemplary embodiment, the processor of the information processing apparatus 10 executes a program stored in the memory, thereby implementing a function of the information processing apparatus 10. The information processing apparatus 10 may have a CPU, a GPU, and an application specific integrated circuit (ASIC) that are each dedicated to specific processing. The information processing apparatus 10 may have a field-programmable gate array (FPGA) where specific processing or all kinds of processing may be programmed.

The information processing apparatus 10 may be connected to the operation unit 36 and the display unit 37. The operation unit 36 is configured of, for example, a keyboard and a mouse. The operation unit 36 inputs an instruction from a user into the information processing apparatus 10. The display unit 37 displays information, based on control from the information processing apparatus 10. Further, the display unit 37 provides an interface for accepting an instruction from the user, based on control from the information processing apparatus 10. The display unit 37 is, for example, a liquid crystal display. The operation unit 36 and the display unit 37 may be integrated into a touch panel display.

Figure 2:
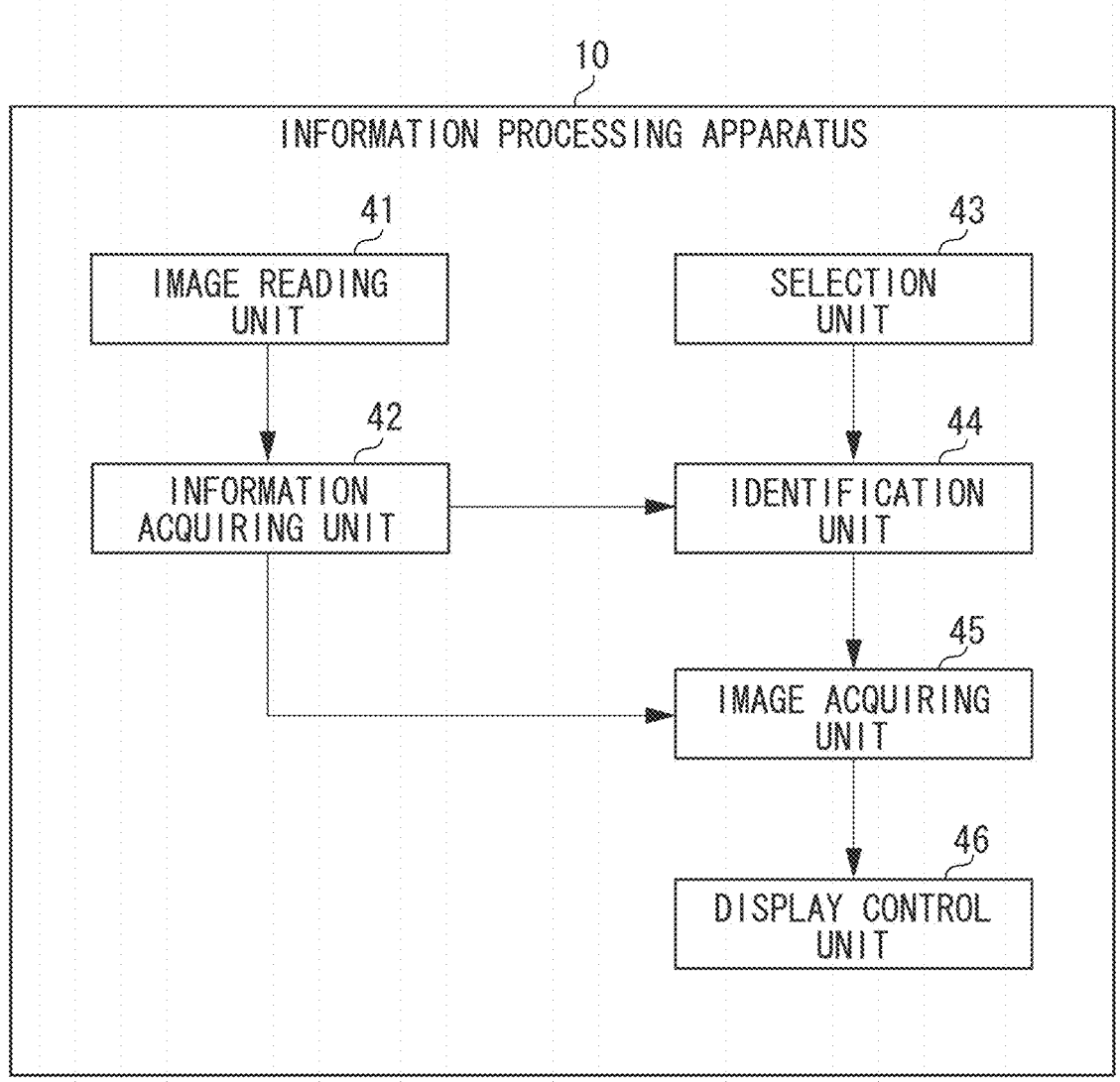
FIG. 2 illustrates an example of a functional configuration of an information processing apparatus according to an exemplary embodiment of the present disclosure.

FIG. 2 illustrates an example of a functional configuration of the information processing apparatus 10 according to the first exemplary embodiment. The information processing apparatus 10 includes an image reading unit 41, an information acquiring unit 42, a selection unit 43, an identification unit 44, an image acquiring unit 45, and a display control unit 46.

The image reading unit 41 acquires a medical image from the database 22 via the communication IF 31 and the LAN 21, based on operation input of the user.

A plurality of two-dimensional images is included in a three-dimensional image acquired by the image reading unit 41 from the database 22. For each of these two-dimensional images, the information acquiring unit 42 acquires information about an orientation of an object and information about a position in the object of the two-dimensional image. The information about the orientation of the object is information about a direction toward the object of the two-dimensional image. Based on the information about the position in the object of the two-dimensional image, the information acquiring unit 42 acquires information about a position where the two-dimensional image included in the three-dimensional image is present. In this aspect, the information acquiring unit 42 is an example of an acquiring unit. Further, the information acquiring unit 42 determines whether a direction toward an object of a two-dimensional image included in each of a plurality of three-dimensional images is the same.

The selection unit 43 selects a three-dimensional image from among three-dimensional images acquired by the image reading unit 41 from the database 22, based on a user instruction input from the operation unit 36. Specifically, the selection unit 43 selects a three-dimensional image to be an interlocking target for processing for specifying a position of a two-dimensional image displayed at the display unit 37.

The identification unit 44 identifies a three-dimensional image for displaying a two-dimensional image at the display unit 37, based on a position specified by the user. In this aspect, the identification unit 44 is an example of a first identification unit. Further, the identification unit 44 identifies a two-dimensional image to be displayed at the display unit 37, from among two-dimensional images included in a three-dimensional image. More specifically, based on information about a position where a two-dimensional image included in a three-dimensional image is present, and an instruction about a position of a two-dimensional image to be displayed at the display unit 37, the identification unit 44 identifies the two-dimensional image to be displayed at the display unit 37. In this aspect, the identification unit 44 is an example of a second identification unit.

The image acquiring unit 45 acquires a two-dimensional image corresponding to a position identified by the identification unit 44, by reading the two-dimensional image from the storage unit 34, for each of a plurality of three-dimensional images.

The display control unit 46 controls the display unit 37 to display information. The display control unit 46 displays, for example, a two-dimensional image acquired for each of a plurality of three-dimensional images, at the display unit 37. These two-dimensional images are arranged when displayed. The display control unit 46 is an example of a display control unit.

The units described throughout the present disclosure are exemplary and/or preferable modules for implementing processes described in the present disclosure. The term "unit", as used herein, may generally refer to firmware, software, hardware, or other component, such as circuitry or the like, or any combination thereof, that is used to effectuate a purpose. The modules can be hardware units (such as circuitry, firmware, a field programmable gate array, a digital signal processor, an application specific integrated circuit, or the like) and/or software modules (such as a computer readable program or the like). The modules for implementing the various steps are not described exhaustively above. However, where there is a step of performing a certain process, there may be a corresponding functional module or unit (implemented by hardware and/or software) for implementing the same process. Technical solutions by all combinations of steps described and units corresponding to these steps are included in the present disclosure.

Figure 3:
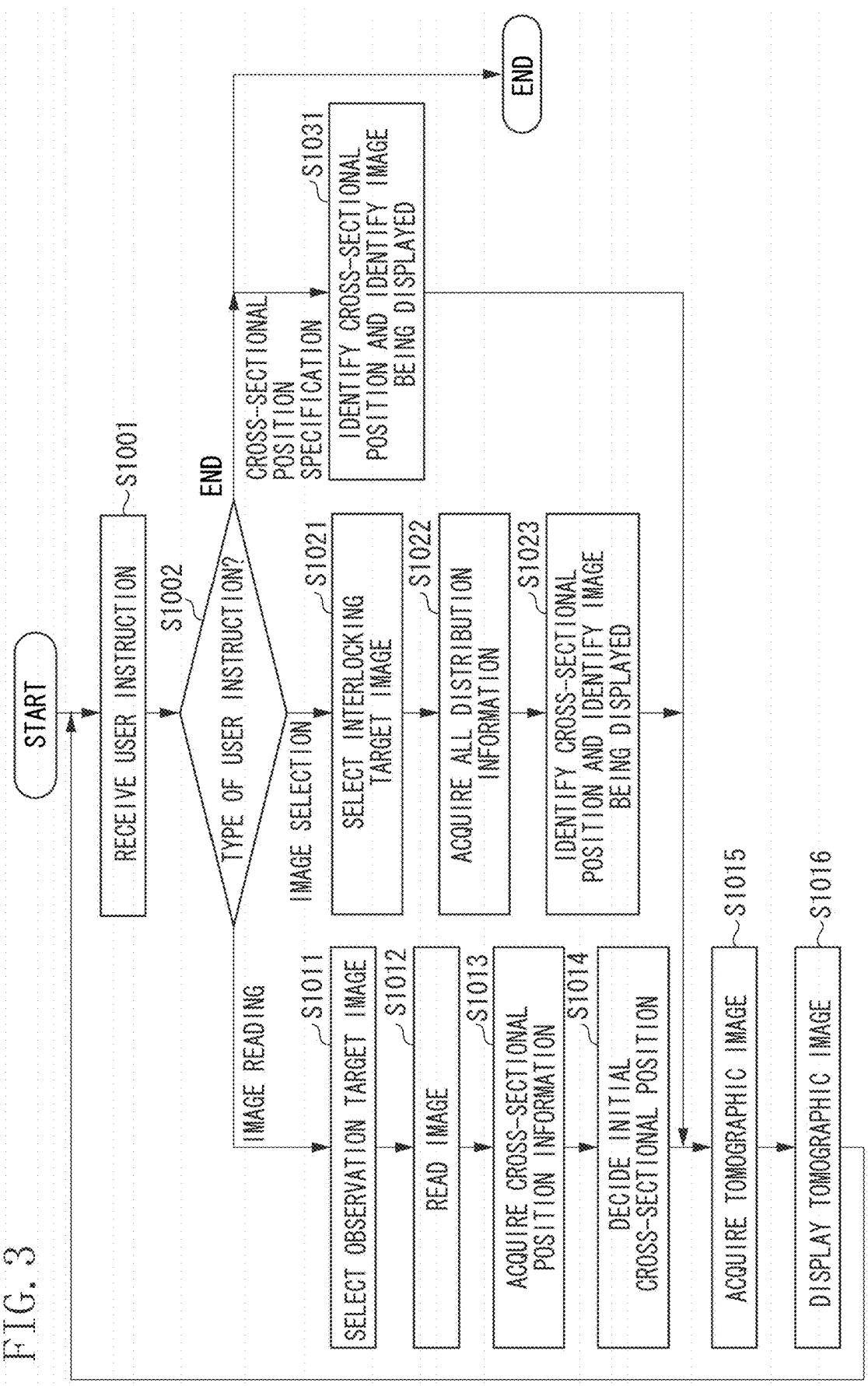
FIG. 3 is a flowchart illustrating an example of processing to be performed by an information processing apparatus according to an exemplary embodiment of the present disclosure.

FIG. 3 is a flowchart illustrating an example of processing to be performed by the information processing apparatus 10. The control unit 35 implements each step in the following processing, unless otherwise specified.

A medical image conforming to Digital Imaging and Communications in Medicine (DICOM) is used in the following description. DICOM is a standard defining a format of medical images, and a communication protocol between apparatuses that process these images. Data conforming to DICOM may be hereinafter referred to as a DICOM object. For example, a medical image, which is a DICOM object, is made up of an area for recording image data and an area for recording meta data. The meta data includes an element identified by a tag. The area for recording the meta data includes, for example, information about an imaging apparatus by which a medical image is acquired, information about an object (a patient), and information about an imaging region. The information about the imaging region is, for example, information for identifying an anatomical part of an object of an acquired medical image. The information about the imaging region may be expressed by a numerical value such as a distance from a specific anatomic structure of the object such as a clavicle. A medical image that does not conform to DICOM may be used, if the medical image is an image from which information similar to information to be described below is obtainable.

In step S1001, the control unit 35 acquires information about operation input performed by the user via the operation unit 36. The user can perform various kinds of operation input for the information processing apparatus 10. Here, a case is described where the user provides an instruction for specifying a plurality of three-dimensional images, and displaying a two-dimensional image included in each of the plurality of three-dimensional images at the display unit 37 while establishing correspondences, and this instruction is received. In this aspect, in step S1001, the control unit 35 receives operation input for any one of an instruction for reading a three-dimensional image, an instruction for selecting a three-dimensional to be an operation target, an instruction for specifying a position of a two-dimensional image (a tomographic image) included in a three-dimensional image, and an instruction for ending a series of steps illustrated in FIG. 3. These instructions are provided, for example, via an interface displayed at the display unit 37.

In step S1002, the processing is divided into branches, according to the content of the user instruction received in step S1001. In a case where the instruction from the user is an instruction for reading a three-dimensional image (image reading), the processing proceeds to step S1011. In a case where the instruction from the user is an instruction for selecting a three-dimensional image to be an operation target (image selection), the processing proceeds to step S1021. In a case where the instruction from the user is an instruction for specifying a position of a two-dimensional image, i.e., a tomographic image, included in a three-dimensional image (cross-sectional position specification), the processing proceeds to step S1031. In a case where the instruction from the user is an instruction for ending, the processing of the example illustrated in FIG. 3 ends.

The information processing apparatus 10 performs step S1011 to step S1016, in a case where an instruction for reading a three-dimensional image is provided by the user in step S1001 (image reading).

In step S1011, the user performs operation input for specifying one or more medical images to be an observation target, i.e., to be displayed at the display unit 37. The control unit 35 acquires information about the operation input performed by the user via the operation unit 36. A case where the user specifies a plurality of three-dimensional images as an observation target will be described below as an example. The image to be the observation target may be one, and may not be a three-dimensional image.

In step S1012, the image reading unit 41 acquires the medical images selected in step S1011 from the database 22, and stores the acquired medical images into the storage unit 34. If the capacity of the RAM 33 is large enough, the image reading unit 41 may store the medical images acquired from the database 22 into the RAM 33.

In step S1013, the information acquiring unit 42 acquires a data configuration and attribute information for each of the plurality of three-dimensional images stored in the storage unit 34 (or the RAM 33). The information acquiring unit 42 determines whether the three-dimensional image has a data configuration including a plurality of two-dimensional images (tomographic images). In a case where the three-dimensional image has a data configuration including a plurality of two-dimensional images, the information acquiring unit 42 acquires attribute information about each of the two-dimensional images. The attribute information is, for example, information indicating a characteristic of an element (a tag) which is a component of a DICOM object. Examples of the attribute information in DICOM include the following information. There is a patient orientation value or an image orientation (patient) value, as information indicating an orientation of an object (a patient). Further, there is an image position (patient) value or a slice location value, as information indicating a position of an object (a patient). Based on the information indicating the orientation of the object in the attribute information, information indicating an orientation of an object to be visualized in each of the two-dimensional images is obtained. In addition, based on the information indicating the position of the object, information indicating a position of each of the two-dimensional images with reference to a reference point of the object is obtained. This position is expressed, for example, in millimeters. In other words, based on the information about the direction in the object (the orientation of the object) of the two-dimensional image included in the three-dimensional image, which is the medical image selected in step S1011 and read in step S1012, the information acquiring unit 42 acquires information about a range of positions of the two-dimensional images included in the three-dimensional image.

Further, based on the information about the orientation and the position of the object visualized in each of the two-dimensional images, the information acquiring unit 42 determines whether the two-dimensional images are tomographic images forming one three-dimensional image. Assume that the orientation of the object in each of the two-dimensional images is the same, and a value indicating the position of each of the two-dimensional images is each of values that can be sequentially arranged, i.e., values in a magnitude relationship. In this case, the information acquiring unit 42 determines that the two-dimensional images are tomographic images included in one three-dimensional image. Assume that the orientation of the object in each of the two-dimensional image is not the same, or a value indicating the position of each of the two-dimensional images is not each of values that can be sequentially arranged. In this case, the information acquiring unit 42 determines that the two-dimensional images are not tomographic images included in one three-dimensional image. For each of the plurality of three-dimensional images, the information acquiring unit 42 acquires the information about the orientation of each of the tomographic images included in the three-dimensional image and the information (distribution information) about the position of each of the tomographic images, by performing the above-described processing. The information acquiring unit 42 stores into the RAM 33 the orientation information and the distribution information about the tomographic image acquired for each of the plurality of three-dimensional images.

In a case where each of the two-dimensional images is a DICOM object, the information acquiring unit 42 may acquire the attribute information about each of the two-dimensional images from a DICOM tag of each of the two-dimensional images. Further, in a case where one DICOM object includes a plurality of two-dimensional images, the information acquiring unit 42 may acquire the attribute information about each of the two-dimensional images from a DICOM tag of the one DICOM object. Furthermore, in the first exemplary embodiment, in a case where the medical image selected in step S1011 and read in step S1012 does not include a plurality of two-dimensional images, the medical image is not a processing target in and after step S1021 to be described below.

In step S1014, based on a predetermined rule, the identification unit 44 decides a cross-sectional position to be initially displayed (hereinafter referred to as an initial display cross-sectional position) in each of the plurality of three-dimensional images. For example, assume that the respective cross-sectional positions of tomographic images included in a three-dimensional image are distributed in a direction from the head side toward the foot side (caudal). In this case, the cross-sectional position of a tomographic image closest to the head is the initial display cross-sectional position of the three-dimensional image. Further, for example, assume that the respective cross-sectional positions of tomographic images included in a three-dimensional image are distributed in a direction from the stomach side (the front face) to the back side. In this case, the cross-sectional position of a tomographic image closest to the front of the stomach is the initial display cross-sectional position of the three-dimensional image. Furthermore, for example, assume that the respective cross-sectional positions of tomographic images included in a three-dimensional image are distributed in a lateral direction of a body. In this case, the cross-sectional position of the rightmost tomographic image is the initial display cross-sectional position of the three-dimensional image.

In step S1015, for each of the plurality of three-dimensional images, the image acquiring unit 45 acquires a tomographic image corresponding to the initial display cross-sectional position decided in step S1014, by reading this tomographic image from the image data stored into the storage unit 34 in step S1012.

In step S1016, the display control unit 46 displays, at the display unit 37, the tomographic image of each of the three-dimensional images, acquired in step S1015. The tomographic images are arranged when displayed. The processing then proceeds to step S1001.

Step S1021 to step S1023 as well as step S1015 and step S1016 are performed in a case where an instruction for selecting a three-dimensional image to be an operation target is provided by the user in step S1001 (image selection).

In step S1021, based on operation input of the user from the operation unit 36, the selection unit 43 selects a three-dimensional image to be an operation target. The control unit 35 may determine that an instruction for image selection has been provided from the user, when operation input for selecting a three-dimensional image has been performed by the user via an interface displayed at the display unit 37. The interface for selecting a three-dimensional image to be an operation target is represented by, for example, checkboxes 131, 132, and 133 illustrated in FIG. 4. For example, the selection unit 43 selects a three-dimensional image where a checkbox is set to ON, in response to operation input for setting the checkbox to ON. Each of a plurality of three-dimensional images selected as the operation target in step S1021 is hereinafter referred to as an interlocking target image. An N-number of interlocking target images In (n=1 to N) are selected by the above-described processing. The selection unit 43 may exclude image data corresponding to unsuccessful acquisition of cross-sectional position information in step S1013, from choices of three-dimensional images to be an operation target.

In step S1022, the information acquiring unit 42 reads an orientation of a tomographic image and distribution information about cross-sectional positions, of each of the interlocking target images selected in step S1021, from the RAM 33. The information acquiring unit 42 may read the information stored into the RAM 33 in step S1013. Further, the information acquiring unit 42 may acquire an orientation of a tomographic image and distribution information about cross-sectional positions of a new interlocking target image specified by the user, in a manner similar to step S1013 described above. In a case where all the interlocking target images are the same in terms of the orientation of the tomographic image, the information acquiring unit 42 determines that the distribution information about the cross-sectional positions of all the interlocking target images is expressed in the same coordinate system.

In a case where some of the interlocking target images are different in terms of the orientation of the tomographic image, the information acquiring unit 42 determines that the distribution information about the cross-sectional positions is expressed in a different coordinate system in some of the interlocking target images. The information acquiring unit 42 displays information for notifying the user of such a result at the display unit 37 via the display control unit 46. Specifically, the information acquiring unit 42 displays information for notifying that the distribution information about the cross-sectional positions is expressed in a different coordinate system in some of the interlocking target images, and these images are not suitable as interlocking target images. In the case where the distribution information about the cross-sectional positions is expressed in a different coordinate system in some of the interlocking target images, the processing may return to step S1021 to display an interface for prompting the user to select an interlocking target image at the display unit 37 via the display control unit 46. The selection unit 43 may automatically exclude, from the interlocking target images, a three-dimensional image expressed in a coordinate system different from the coordinate system of distribution information about cross-sectional positions of a three-dimensional image selected as the first interlocking target image. In other words, the selection unit 43 selects three-dimensional images, which are determined to be the same in terms of a direction toward an object of a two-dimensional image included in a three-dimensional image in step S1013. As a result of the above-described processing, the cross-sectional position distribution information about all the interlocking target images is expressed in the same coordinate system.

The information acquiring unit 42 acquires all distribution information, based on the cross-sectional position distribution information about all the interlocking target images. The all distribution information indicates an overlap between ranges of positions of tomographic images included in each of a plurality of interlocking target images (three-dimensional images), and a cross-sectional spacing of each of the interlocking target images. The information acquiring unit 42 stores the all distribution information into the RAM 33.

Table 1 is an example of the all distribution information. For example, assume that three-dimensional images I1, I2, and I3 are selected as interlocking target images in step S1021. The cross-sectional positions of the image I1 are distributed over a range of −300 mm to 200 mm, and the cross-sectional spacing is 5 mm. The cross-sectional positions of the image I2 are distributed over a range of −490 mm to −150 mm, and the cross-sectional spacing is 2 mm. The cross-sectional positions of the image I3 are distributed over a range of −430 mm to 550 mm, and the cross-sectional spacing is 7 mm. Here, the all distribution information can be expressed as information in a tabular form illustrated in Table 1.

TABLE 1

|  | Image I1 | Image I2 | Image I3 |
| --- | --- | --- | --- |
| Minimum value (mm) of cross-sectional position | −300 | −490 | −430 |
| Maximum value (mm) of cross-sectional position | 200 | −150 | 550 |
| Cross-sectional spacing | 5 | 2 | 7 |

In step S1023, the identification unit 44 sets an initial value of an interlocking display cross-sectional position Pc. The identification unit 44 then decides a display cross-sectional position Pn of each of the interlocking target images In, based on the interlocking display cross-sectional position Pc. Further, the identification unit 44 identifies an image for displaying a tomographic image at the display unit 37, from among the interlocking target images In.

Specifically, first, the identification unit 44 sets the initial value of the interlocking display cross-sectional position Pc. For example, at the time when the interlocking target image is selected first in step S1021, a display cross-sectional position of the interlocking target image is displayed at the display unit 37, and the identification unit 44 sets the display cross-sectional position as the interlocking display cross-sectional position Pc. In a case where the interlocking target images I1, I2, and I3 are selected in this order, the identification unit 44 sets a display cross-sectional position P1 of the interlocking target image I1, as the interlocking display cross-sectional position Pc.

Next, the identification unit 44 identifies the display cross-sectional position Pn of each of the interlocking target images In, based on the initial value of the interlocking display cross-sectional position Pc. The identification unit 44 determines whether the interlocking display cross-sectional position Pc is present within the cross-sectional range in each of the interlocking target images In. Assume that the identification unit 44 determines that the interlocking display cross-sectional position Pc is outside the cross-sectional range of an interlocking target image. In this case, the identification unit 44 sets an invalid value as the display cross-sectional position Pn of the interlocking target image. Assume that the identification unit 44 determines that the interlocking display cross-sectional position Pc is within the cross-sectional range of an interlocking target image. In this case, the identification unit 44 decides a cross-sectional position at a position nearest to the interlocking display cross-sectional position Pc in the interlocking target image, as the display cross-sectional position Pn of the interlocking target image. Assume that there are two cross-sectional positions nearest to the display cross-sectional position P1 among the cross-sectional positions of an interlocking target image. In this case, for example, the identification unit 44 selects a smaller cross-sectional position, based on predetermined priorities. The identification unit 44 sets an effective value as a display cross-sectional position, and identifies an interlocking target image for displaying a tomographic image at the display unit 37. In other words, the identification unit 44 sets an invalid value as a display cross-sectional position, and identifies an interlocking target image for not displaying a tomographic image at the display unit 37. In a case of P1=−300 mm in the above-described example, P1=−300 mm, P2=−300 mm, and P3=−297 mm are assumed. In a case of P1=−295 mm in the above-described example, P1=−295 mm, P2=−296 mm, and P3=−297 mm are assumed. In a case of P1=100 mm in the above-described example, P1=100 mm, P2=(an invalid value), and P3=102 mm are assumed. Finally, the identification unit 44 stores the identified display cross-sectional position Pn of each of the interlocking target images In, into the RAM 33.

In step S1015 following step S1023, the image acquiring unit 45 acquires a tomographic image corresponding to each of the display cross-sectional positions Pn identified in step S1023. In a case where an invalid value is set as the display cross-sectional position in step S1023, the image acquiring unit 45 does not acquire a tomographic image of the medical image concerned.

In step S1016, the display control unit 46 displays the tomographic image acquired in step S1015, at the display unit 37. With respect to a medical image for which an invalid value is set as the display cross-sectional position in step S1023, and a tomographic image is not acquired in step S1015, the display control unit 46 displays no tomographic image at the display unit 37. In other words, the display unit 37 displays a tomographic image at each of positions interlocked between medical images, in each of which a range of positions of two-dimensional images includes a cross-sectional position specified by a display instruction from the user, among a plurality of medical images.

Step S1031 as well as step S1015 and step S1016 are performed in a case where an instruction for specifying a position of a two-dimensional image, i.e., a tomographic image, included in a three-dimensional image is provided in step S1001 (cross-sectional position specification).

In step S1031, the identification unit 44 acquires an instruction for specifying (updating) a display cross-sectional position of each of the three-dimensional images, from the operation unit 36. The user performs operation input in, for example, a screen in FIG. 4 to be described below, via the operation unit 36. The tomographic image displayed in each of the three-dimensional images, which are interlocking target images, is thereby changed. Examples of the instruction for updating the display cross-sectional position include an instruction for moving the display cross-sectional position forward by a predetermined amount (shifting in a positive direction by a predetermined amount). The examples further include an instruction for moving the display cross-sectional position backward by a predetermined amount (shifting in a negative direction by a predetermined amount), and an instruction for directly specifying a specific display cross-sectional position. The examples of the instruction for updating the display cross-sectional position may further include an instruction for automatically moving the display cross-sectional position forward by a predetermined amount periodically, and an instruction for automatically moving the display cross-sectional position backward by a predetermined amount periodically. The identification unit 44 automatically updates the display cross-sectional position periodically, by using a timer included in the control unit 35.

In the case where the instruction for updating the display cross-sectional position is input from the operation unit 36, the identification unit 44 reads the display cross-sectional position Pn and the all distribution information set in each of the interlocking target images, from the RAM 33. The identification unit 44 then acquires a new display cross-sectional position Pn' in response to the input instruction. Specifically, for example, assume that the instruction for moving the display cross-sectional position forward by a predetermined amount is provided. In this case, the identification unit 44 acquires a temporary display cross-sectional position Pn' of each of the interlocking target images, by adding the cross-sectional spacing of the interlocking target image to the display cross-sectional position Pn set in the interlocking target image. Assume that, for example, the instruction for moving the display cross-sectional position backward by a predetermined amount is provided. In this case, the identification unit 44 acquires a temporary display cross-sectional position Pn' of each of the interlocking target images, by subtracting the cross-sectional spacing of the interlocking target image from the display cross-sectional position Pn set in the interlocking target image. Assume that, for example, the interlocking target images have the respective display cross-sectional positions of P1=−150 mm, P2=−150 mm, and P3=−150 mm. In this case, new temporary display cross-sectional positions P1', P2', and P3' are calculated as follows.

(a) In a case where an instruction for moving the display cross-sectional position forward by a predetermined amount is acquired:

$P1'=-150$ mm+5 mm=−145 mm $P2'=-150$ mm+2 mm=−148 mm $P3'=-150$ mm+7 mm=−143 mm (b) In a case where an instruction for moving the display cross-sectional position backward by a predetermined amount is acquired:

$P1'=-150$ mm−5 mm=−155 mm $P2'=-150$ mm−2 mm=−152 mm $P3'=-150$ mm−7 mm=−157 mm

Next, the identification unit 44 determines whether each of the temporary display cross-sectional positions Pn' is within the cross-sectional range of the interlocking target image corresponding thereto. The identification unit 44 makes this determination by referring to the cross-sectional range (the range between the minimum value and the maximum value of the cross-sectional positions) of each of the interlocking target images included in the all distribution information. In a case where the identification unit 44 determines that the temporary display cross-sectional position Pn' is outside the cross-sectional range of an interlocking target image, the identification unit 44 sets an invalid value as the display cross-sectional position Pn of this interlocking target image. From among the temporary display cross-sectional positions Pn' determined to be within the cross-sectional range of each of the interlocking target images, the identification unit 44 selects the smallest cross-sectional position in the case of the instruction (a), and the largest cross-sectional position in the case of the instruction (b). The identification unit 44 then decides the selected cross-sectional position as the interlocking display cross-sectional position Pc. For example, assume that the temporary display cross-sectional positions P1' and P3' are determined to be within the respective cross-sectional ranges in the above-described example (a). In this case, the display cross-sectional position P1' is selected as the smallest cross-sectional position. Therefore, the interlocking display cross-sectional position Pc is −145 mm. Assume that the temporary display cross-sectional positions P1', P2', and P3' are determined to be within the respective cross-sectional ranges in the above-described example (b). In this case, the display cross-sectional position P2' is selected as the largest cross-sectional position. Therefore, the interlocking display cross-sectional position Pc is −152 mm.

Assume that a predetermined amount (each of the cross-sectional spacings) is (a) added to or (b) subtracted from the display cross-sectional position at the time when the instruction for updating the display cross-sectional position is provided. In either case, the cross-sectional position of the image I2 corresponding to the smallest cross-sectional spacing takes (a) the minimum value or (b) the maximum value. In this aspect, the identification unit 44 identifies the display cross-sectional position of the interlocking target image, according to the smallest cross-sectional spacing of the medical image, among the interlocking target images. Further, assume that the tomographic image of the medical image of the smallest cross-sectional spacing reaches the upper end or the lower end, thereby preventing the display cross-sectional position from being further updated. In this case, the identification unit 44 identifies the display cross-sectional position of the interlocking target image, according to the smallest cross-sectional spacing of the medical image, among the interlocking target images in which the tomographic images are present.

In a case where an instruction for directly specifying a specific display cross-sectional position is input, the identification unit 44 sets the display cross-sectional position Pn of each of the interlocking target images In, based on the specified display cross-sectional position (Pd). First, the identification unit 44 determines whether the display cross-sectional position Pd is within the cross-sectional range of each of the interlocking target images. In the interlocking target image for which the display cross-sectional position Pd is determined to be within the range, the identification unit 44 identifies a cross-sectional position Pn' nearest to the display cross-sectional position Pd. The identification unit 44 then identifies the interlocking display cross-sectional position Pc based on the cross-sectional position Pn'. For example, the identification unit 44 determines that a cross-sectional position Pn' nearest to the display cross-sectional position Pd among all the cross-sectional positions Pn' is the interlocking display cross-sectional position Pc. Alternatively, in the interlocking target image of the smallest cross-sectional spacing among the interlocking target images for which the display cross-sectional position Pd is determined to be within the cross-sectional range, the identification unit 44 may determine that a cross-sectional position Pn' nearest to the display cross-sectional position Pd is the interlocking display cross-sectional position Pc.

Furthermore, the identification unit 44 identifies the display cross-sectional position Pn for all the interlocking target images In, based on the interlocking display cross-sectional position Pc. The identification unit 44 performs processing by replacing the initial value of the interlocking display cross-sectional position Pc set in step S1023 with the interlocking display cross-sectional position Pc described above. In the above-described example (a), the interlocking display cross-sectional position Pc=−145 mm is provided and thus, new display cross-sectional positions are P1=−145 mm, P2=(an invalid value), and P3=−143 mm. On the other hand, in the above-described example (b), the interlocking display cross-sectional position Pc=−152 mm is provided and thus, new display cross-sectional positions are P1=−150 mm, P2=−152 mm, and P3=−150 mm. The identification unit 44 stores the updated display cross-sectional position Pn of each of the interlocking target images In into the RAM 33.

The operation input for specifying the display cross-sectional position in step S1031 is performed by the user, for an arbitrary interlocking target image. In other words, an instruction may be provided based on operation input for an interlocking target image, for which the display cross-sectional position is not included in the cross-sectional range and no tomographic image is displayed. In this case, as well, the above-described processing is performed based on the cross-sectional position of the tomographic image displayed at the time when the instruction is provided. When acquiring the temporary display cross-sectional position of an interlocking target image for which an invalid value is set as the display cross-sectional position, the identification unit 44 adds or subtracts a predetermined amount to or from the minimum value or the maximum value of the cross-sectional position of this interlocking target image.

Step S1015 following step S1031 is similar to step S1015 following step S1023, and therefore will not be described in detail by incorporating the above description. When the display cross-sectional position Pn is updated in step S1031, the image acquiring unit 45 acquires a tomographic image corresponding to the display cross-sectional position Pn acquired in step S1031. The image acquiring unit 45 does not acquire the tomographic image of the medical image for which an invalid value is set as the display cross-sectional position Pn in step S1031.

In step S1016, the display control unit 46 displays the tomographic image, which is acquired in step S1015 and corresponds to the cross-sectional position updated in step S1031, at the display unit 37.

Figure 4:
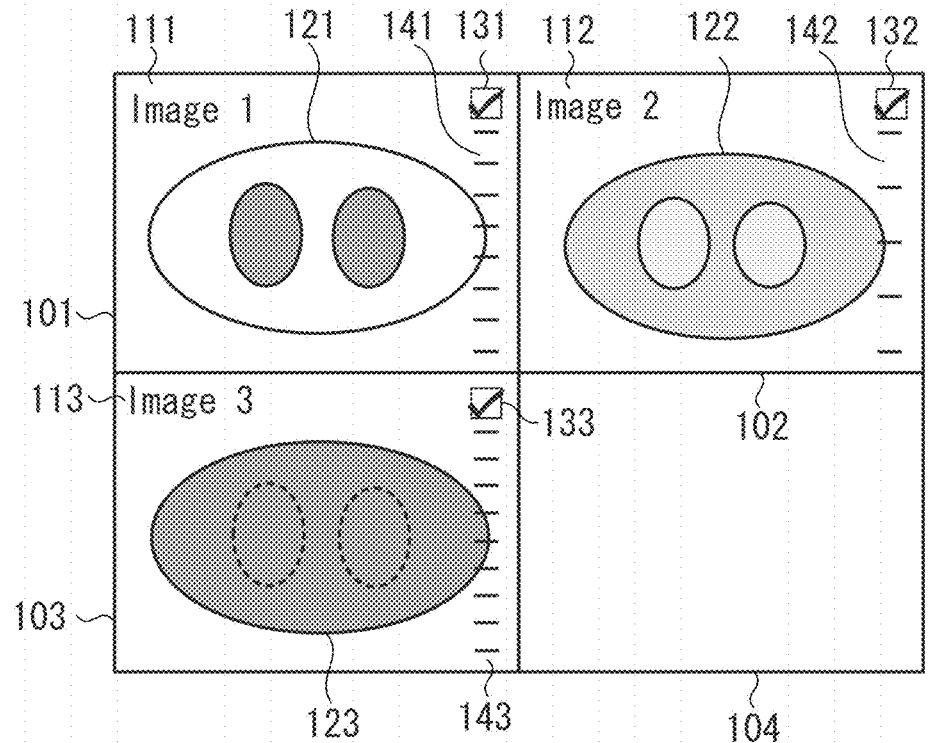
FIG. 4 illustrates an example of a screen displayed at a display unit by an information processing apparatus according to an exemplary embodiment of the present disclosure.

FIG. 4 illustrates an example of a screen displayed at the display unit 37. The screen illustrated in FIG. 4 will be hereinafter referred to as a first screen. The first screen includes, for example, medical-image display areas 101, 102, 103, and 104.

For example, assume that medical images 1, 2, and 3 (hereinafter may be referred to as images I1, I2, and I3) are each specified as a medical image to be an observation target in step S1011. This case will be described as an example. The respective specified medical images are displayed in the medical-image display areas 101, 102, and 103. Image identification information pieces 111, 112, and 113, tomographic images 121, 122, and 123, checkboxes 131, 132, and 133, and cross-sectional position display scales 141, 142, and 143, respectively, are displayed in the medical-image display areas 101, 102, and 103. The operation input by the user to select the interlocking target image in step S1012 is to mark these checkboxes. The display control unit 46 may prohibit the information acquiring unit 42 from selecting a checkbox of a three-dimensional image in which the orientation of an object does not coincide with those of other interlocking target images.

A case where the medical images 1, 2, and 3 are each selected as an interlocking target image will be described below as an example. Assume that the medical images 1, 2, and 3 correspond to the images I1, I2, and I3 in Table 1, and each have the cross-sectional range and the cross-sectional spacing listed in Table 1.

The user moves the mouse thereby moving a cursor displayed at the display unit 37, onto a medical-image display area (here, any one of the areas 101, 102, and 103) in which an interlocking target image is displayed. The user then drags the mouse while pressing the left button of the mouse. The identification unit 44 decides a direction and an amount for changing the interlocking display cross-sectional position, based on a moving amount of the mouse in a vertical direction. Here, operation for dragging the mouse upward is the operation input for shifting the display cross-sectional position in the negative direction, and operation for dragging the mouse downward is the operation input for shifting the display cross-sectional position in the positive direction. In another example, the user rotates a wheel of the mouse on the display area of a medical image in which an arbitrary interlocking target image is displayed. Based on a rotation direction and a rotation amount of the mouse wheel, the identification unit 44 decides a direction and an amount for changing the interlocking display cross-sectional position. The identification unit 44 thus decides a new interlocking display cross-sectional position.

In the first exemplary embodiment, dragging operation or operation for rotating the wheel of the mouse may be performed on the medical image in which no tomographic image is displayed at the display unit 37 as described above. This operation is also processed as the instruction for updating the display cross-sectional position.

The user may press up and down arrow keys of the keyboard that is an example of the operation unit 36. The identification unit 44 decides a direction for changing the interlocking display cross-sectional position, based on a pressed direction of the up and down arrow keys. Each time one of the up and down arrow keys is pressed, the identification unit 44 changes the interlocking display cross-sectional position by a predetermined amount.

Upon receipt of an instruction for changing the interlocking display cross-sectional position through operation input of the user, the identification unit 44 decides a new interlocking display cross-sectional position. The display control unit 46 updates the content to be displayed at the display unit 37, based on the new interlocking display cross-sectional position. In the example illustrated in FIG. 4, the display control unit 46 updates each of the tomographic images 121, 122, and 123 of the interlocking target images I1, I2, and I3, to a tomographic image corresponding to the new interlocking display cross-sectional position. In other words, the display control unit 46 displays a tomographic image, which is a two-dimensional image at a position corresponding to the position specified by the user, at the display unit 37. Further, the display control unit 46 displays a specification section indicating the position specified by the user.

In the first screen, the images I1, I2, and I3 are each specified as an interlocking target image. Among these images, the image I2 has the smallest cross-sectional spacing. Therefore, the display cross-sectional position is updated according to the cross-sectional spacing of the image I2, and a tomographic image corresponding to the updated display cross-sectional position is displayed.

Figure 5:
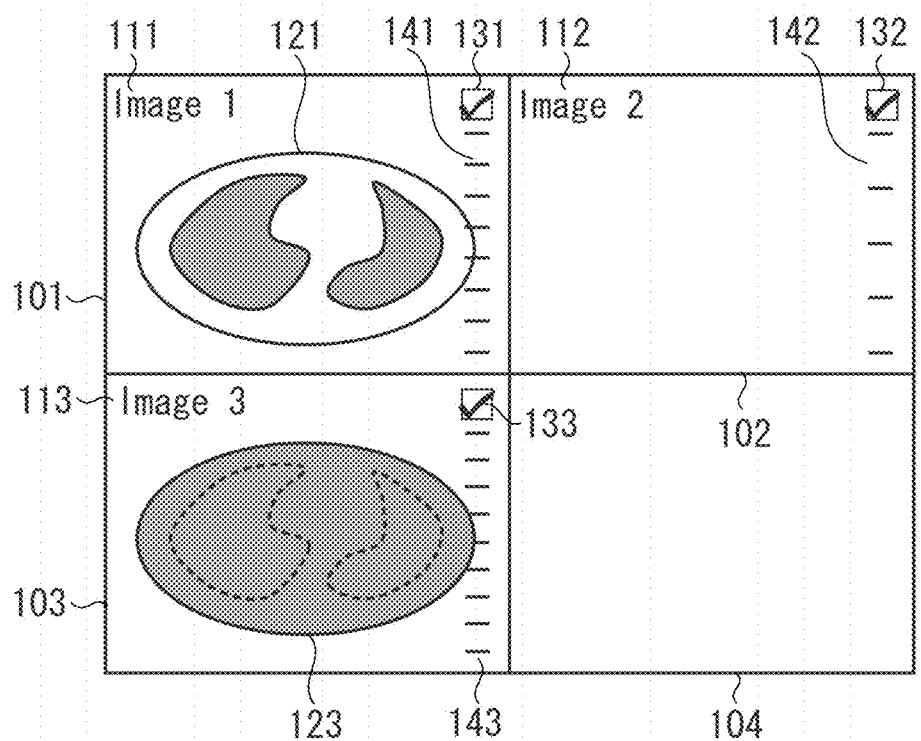
FIG. 5 illustrates an example of a screen displayed at a display unit by an information processing apparatus according to an exemplary embodiment of the present disclosure.

FIG. 5 illustrates an example of a screen displayed at the display unit 37. The screen illustrated in FIG. 5 will be hereinafter referred to as a second screen. A configuration similar to that of the first screen is provided with a similar sign, and detailed description thereof will be omitted here by incorporating the above description.

The second screen is displayed at the display unit 37, in a case where the display cross-sectional position is a value of more than −149.0 mm and 202.5 mm or less, in the example in Table 1. In this case, an interlocking target image in which a tomographic image is present is each of the images I1 and I3. Therefore, the tomographic images 121 and 123 are displayed in the display areas 101 and 103, respectively, while no tomographic image is displayed in the medical-image display area 102.

In the second screen, a medical image including a displayable cross-sectional position among the interlocking target images is each of the images I1 and I3. Among these images, the image I1 has the smallest cross-sectional spacing. Therefore, the display cross-sectional position is updated according to the cross-sectional spacing of the image I1, and a tomographic image corresponding to the updated display cross-sectional position is displayed.

Figure 6:
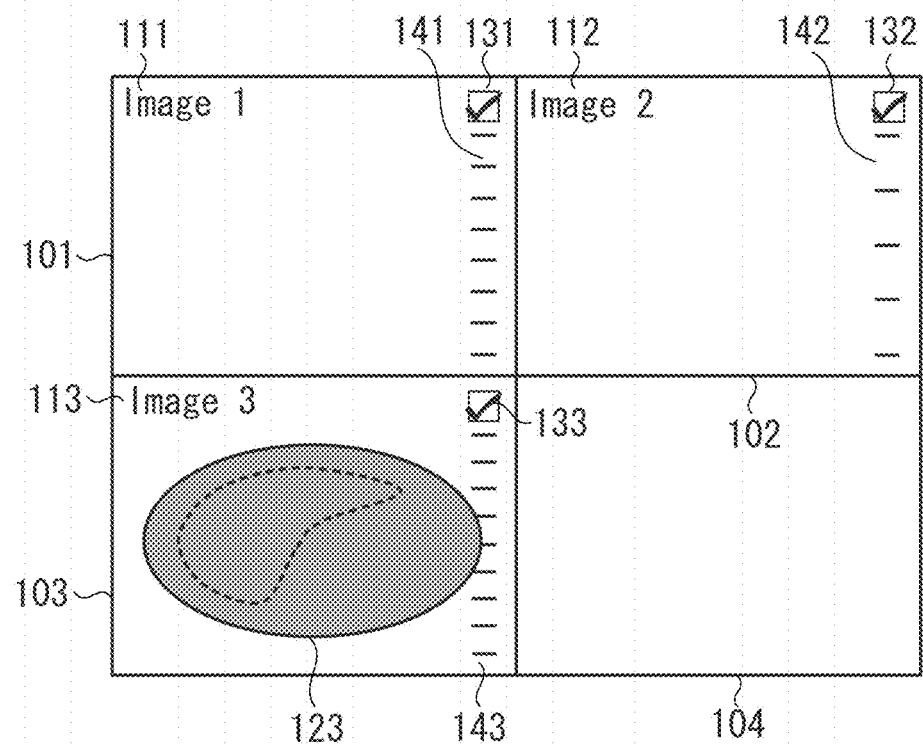
FIG. 6 illustrates an example of a screen displayed at a display unit by an information processing apparatus according to an exemplary embodiment of the present disclosure.

FIG. 6 illustrates an example of a screen displayed at the display unit 37. The screen illustrated in FIG. 6 will be hereinafter referred to as a third screen. A configuration similar to that of the first screen is provided with a similar sign, and detailed description thereof will be omitted here by incorporating the above description.

The third screen is displayed at the display unit 37, in a case where the display cross-sectional position is a value of more than 202.5 mm and 553.5 mm or less, in the example in Table 1. In this case, an interlocking target image in which a tomographic image is present is the image I3. Therefore, the tomographic image 123 is displayed in the display area 103, while no tomographic image is displayed in each of the medical-image display areas 101 and 102.

In the third screen, a medical image including a displayable cross-sectional position among the interlocking target images is the image I3. Therefore, the display cross-sectional position is updated according to the cross-sectional spacing of the image I3, and a tomographic image corresponding to the updated display cross-sectional position is displayed.

As described above, according to the information processing apparatus of the first exemplary embodiment, it is possible to display the respective two-dimensional images included in the plurality of three-dimensional images while establishing correspondences, by simple operation. In particular, even in a range including no two-dimensional image of some of the three-dimensional images, it is possible to keep displaying the two-respective dimensional images included in the other three-dimensional images while establishing correspondences. In another respect, in a case where the respective two-dimensional images included in the three or more three-dimensional images are displayed while correspondences are established, the information processing apparatus according to the first exemplary embodiment changes the combination of the three-dimensional images for displaying the two-dimensional images, based on the cross-sectional position to be displayed. Further, in the first exemplary embodiment, the displayed position can be updated according to the spacing (cross-sectional spacing) of the positions of the two-dimensional images included in the three-dimensional image corresponding to the smallest cross-sectional spacing, among the three-dimensional images that can display the tomographic images. This allows a user such as a doctor, who observes a plurality of three-dimensional images while performing a comparison, can make observations without missing a part of a two-dimensional image included in a three-dimensional image. The first exemplary embodiment provides a particular manner of information processing that improves over the art.

Variation Example 1 of First Exemplary Embodiment

In the first exemplary embodiment, the case where the user selects the interlocking target image in step S1021 has been described as an example, but the present disclosure is not limited to this example. For example, the selection unit 43 may automatically set all interlockable three-dimensional images, as interlocking target images. In another example, the selection unit 43 may set a three-dimensional image that meets a predetermined condition, as an interlocking target image. In step S1021, the user may be allowed to select an image not to be interlocked. In another example, in step S1021, the selection unit 43 may select a three-dimensional image according to input such as operation input of the user, from among a plurality of three-dimensional images being the same in terms of a direction toward an object of a two-dimensional image included in each of the three-dimensional images.

Examples of the condition for selecting an interlocking target image include a condition that three-dimensional images are in the same coordinate system, a condition that a plurality of sequence images are captured in the same inspection, and a condition that images are captured under the same inspection condition. The selection unit 43 acquires the above-described information for selecting an interlocking target image, by reading, for example, information recorded in the DICOM header portion of each image as the attribute information about image.

In another example, the selection unit 43 is provided to interlock a group of a plurality of images, which is subjected to processing for registration between images, and for which a positional correspondence relation between images is stored as explicit information. In this case, preferably, the corresponding tomographic images calculated based on registration information are displayed in an interlocking manner. In step S1022, the information acquiring unit 42 selects one interlocking target image as a reference image, from among the registered images. Next, the information acquiring unit 42 calculates the cross-sectional range and the cross-sectional spacing of each of the other interlocking target images, by converting the coordinate system of each of the other interlocking target images into the coordinate system of the reference image by using the registration information. The information acquiring unit 42 calculates the all distribution information, from the cross-sectional range and the cross-sectional spacing of the reference image, and the cross-sectional range and the cross-sectional spacing of each of the other interlocking target images. Further, in step S1015, the image acquiring unit 45 identifies a cross-sectional position nearest to the interlocking display cross-sectional position Pc in each of the interlocking target images, based on the registration information. The image acquiring unit 45 acquires a tomographic image located at a position (a cross-sectional position P') nearest to the identified cross-sectional position. In this way, in a case where information about registration is available, corresponding cross sections between the images can be displayed in an interlocking manner with high accuracy. The information about registration may be in any form such as translation information, affine conversion information, and application information about deformation field between images.

Variation Example 2 of First Exemplary Embodiment

In the first exemplary embodiment, the cross-sectional position information about the interlocking target image is acquired from the attribute information about image recorded in the DICOM header portion, and this case is described as an example. However, the present disclosure is not limited to this example. For example, the information acquiring unit 42 may acquire the cross-sectional position information about the interlocking target image, based on information input by the user via the operation unit 36.

Variation Example 3 of First Exemplary Embodiment

The operation input for specifying the display cross-sectional position is not limited to the above-described example, and may be, for example, operation input using a scroll bar (not illustrated) or the cross-sectional position display scales 141, 142, and 143 illustrated in FIGS. 4 to 6. In this case, the user may specify the display cross-sectional position Pd. Further, a scroll bar (not illustrated) or a cross-sectional position display scale may be set in a range in which a two-dimensional image included in any of all interlocking target images is present, and this scroll bar or display scale may be presented to the user as an interface for the user to specify a display cross-sectional position.

In addition, the method of displaying the tomographic image of each of the plurality of three-dimensional images is not limited to the method of displaying the arranged tomographic images as represented by the example in each of FIGS. 4 to 6. For example, the tomographic images may be superimposed, or may be alternately displayed in a time division manner.

Variation Example 4 of First Exemplary Embodiment

In the first exemplary embodiment, the interlocking display cross-sectional position Pc is identified based on the cross-sectional position to be displayed at the display unit, and this case is described as an example. However, the present disclosure is not limited to this example. For example, the user may select one three-dimensional image, and the interlocking display cross-sectional position Pc may be identified based on the cross-sectional spacing of the selected three-dimensional image. In this case, it is preferable to provide a configuration capable of switching between a mode of performing the processing described in the first exemplary embodiment and a mode of performing processing based on the cross-sectional spacing of the one three-dimensional image selected by the user.

VARIATION EXAMPLES

The present disclosure can also be implemented by such processing that a program for implementing one or more functions of the above-described exemplary embodiment is supplied to a system or apparatus via a network or storage medium. One or more processors in a computerized configuration(s) of the system or apparatus read the program and execute the read program. The present disclosure can also be implemented by a circuit (e.g., ASIC) for implementing one or more functions.

The information processing apparatus in each of the above-described exemplary embodiments may be implemented as a single apparatus, or may be in a form of executing the above-described processing by combining a plurality of apparatuses to be capable of communicating with each other, and both are included in exemplary embodiments of the present disclosure. The above-described processing may be executed in a common server apparatus or server group. A plurality of apparatuses for configuring an information processing apparatus and an information processing system may be sufficient if these apparatuses are capable of communicating at a predetermined communication rate. Further, the plurality of apparatuses is not required to be present in the same facility or the same country.

Exemplary embodiments of the present disclosure include a form in which a system or apparatus is supplied with a software program for implementing the function of the above-described exemplary embodiment, and the computerized configuration(s) of the system or apparatus read(s) a code of the supplied program and execute(s) the read code.

Therefore, a program code itself to be installed onto a computer to implement processing according to an exemplary embodiment in the computerized configuration(s) is an exemplary embodiment of the present disclosure. Further, assume that a program such as an operating system (OS) running on a computer performs part or all of actual processing, based on an instruction included in a program read by the computerized configuration(s). The function of the above-described exemplary embodiment can also be implemented by such processing.

Exemplary embodiments of the present disclosure also include a form implemented by appropriately combining the above-described exemplary embodiments.

Two-dimensional images to be displayed in correspondence with each other among a plurality of three-dimensional images are each identified according to a specified position and a position where the two-dimensional image included in each of the three-dimensional images is present. Therefore, even in a case where a correspondence relation disappears because the position of the two-dimensional image included in one of the three-dimensional images reaches an end portion of a range thereof, the two-dimensional images included in the other three-dimensional images can be displayed in correspondence with each other, based on a correspondence relation between the other three-dimensional images.

Other Embodiments

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, and one or more memories (e.g., central processing unit (CPU), micro processing unit (MPU)), and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™) a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of priority from Japanese Patent Application No. 2017-079435, filed Apr. 13, 2017, which is hereby incorporated by reference herein in its entirety.

What is claimed is:

1. An information processing apparatus comprising:
at least one memory storing instructions; and
at least one processor that when executing the instructions, causes the information processing apparatus to:
acquire, for each of a plurality of three-dimensional images, information about a position where a two-dimensional image included in the three-dimensional image is present;
identify, based on an instruction about a position of a two-dimensional image to be displayed at a display unit, a three-dimensional image to be a target of the instruction; and
identify, based on information about the position specified by the instruction, and the information about the position where the two-dimensional image is present for each of the plurality of three-dimensional images, a two-dimensional image which is included in the identified three-dimensional image, and which is to be displayed at the display unit,
wherein the information processing apparatus identifies a two-dimensional image at a position nearest to the position specified by the instruction, the identified two-dimensional image being included in a three-dimensional image, which has a smallest spacing of the positions at each of which the two-dimensional image included in the three-dimensional image is present, among the identified three-dimensional images.

2. The information processing apparatus according to claim 1, wherein the information processing apparatus identifies a two-dimensional image included in the identified three-dimensional image, based on a position of the two-dimensional image included in the three-dimensional image having the smallest spacing of the positions.

3. The information processing apparatus according to claim 1, wherein the information processing apparatus does not identify a two-dimensional image included in a three-dimensional image, in which the position specified by the instruction is not included in a range of the positions at each of which the two-dimensional image included in the three-dimensional image is present, among the identified three-dimensional images.

4. The information processing apparatus according to claim 1, wherein the at least one processor when executing the instructions further causes the information processing apparatus to display the identified two-dimensional image, at the display unit.

5. The information processing apparatus according to claim 1, wherein a first three-dimensional image and a second three-dimensional image, included in the plurality of three-dimensional images, are three-dimensional images including respective ranges different from each other, and are registered beforehand.

6. An information processing system comprising:
at least one memory storing instructions; and
at least one processor that when executing the instructions, causes the information processing apparatus to:
acquire, for each of a plurality of three-dimensional images, information about a position where a two-dimensional image included in the three-dimensional image is present;
identify, based on an instruction about a position of a two-dimensional image to be displayed at a display unit, a three-dimensional image to be a target of the instruction; and
identify, based on information about the position specified by the instruction, and the information about the position where the two-dimensional image is present for each of the plurality of three-dimensional images, a two-dimensional image which is included in the identified three-dimensional image, and which is to be displayed at the display unit,
wherein a two-dimensional image is identified at a position nearest to the position specified by the instruction, the identified two-dimensional image being included in a three-dimensional image, which has a smallest spacing of the positions at each of which the two-dimensional image included in the three-dimensional image is present, among the identified three-dimensional images.

7. An information processing method comprising:
acquiring, for each of a plurality of three-dimensional images, information about a position where a two-dimensional image included in the three-dimensional image is present;
identifying, based on an instruction about a position of a two-dimensional image to be displayed at a display unit, a three-dimensional image to be a target of the instruction; and
identifying, based on information about the position specified by the instruction, and the information about the position where the two-dimensional image is present for each of the plurality of three-dimensional images, a two-dimensional image which is included in the identified three-dimensional image, and which is to be displayed at the display unit,
wherein a two-dimensional image is identified at a position nearest to the position specified by the instruction, the identified two-dimensional image being included in a three-dimensional image, which has a smallest spacing of the positions at each of which the two-dimensional image included in the three-dimensional image is present, among the identified three-dimensional images.

8. A non-transitory storage medium for causing a computer to execute an information processing method comprising:

acquiring, for each of a plurality of three-dimensional images, information about a position where a two-dimensional image included in the three-dimensional image is present;

identifying, based on an instruction about a position of a two-dimensional image to be displayed at a display unit, a three-dimensional image to be a target of the instruction; and identifying, based on information about the position specified by the instruction, and the information about the position where the two-dimensional image is present for each of the plurality of three-dimensional images, a two-dimensional image which is included in the identified three-dimensional image, and which is to be displayed at the display unit, wherein a two-dimensional image is identified at a position nearest to the position specified by the instruction, the identified two-dimensional image being included in a three-dimensional image, which has a smallest spacing of the positions at each of which the two-dimensional image included in the three-dimensional image is present, among the identified three-dimensional images.

9. An information processing apparatus comprising:
at least one memory storing instructions; and
at least one processor that when executing the instructions, causes the information processing apparatus to:
compare a first spacing that is a spacing of a plurality of two-dimensional images included in a first three-dimensional image, and a second spacing that is a spacing of a plurality of two-dimensional images included in a second three-dimensional image, thereby determining a smaller spacing of the first spacing and the second spacing; and display, based on the determined spacing, the plurality of two-dimensional images included in the first three-dimensional image and the plurality of two-dimensional images included in the second three-dimensional image which are interlocked, at a display unit, according to scroll operation of a user.

10. The information processing apparatus according to claim 9, wherein the at least one processor when executing the instructions further causes the information processing apparatus to identify, based on an instruction about a position of a two-dimensional image to be displayed at the display unit, a three-dimensional image to be a target of the instruction, from among three or more three-dimensional images registered beforehand, wherein a smaller spacing is determined of the first spacing and the second spacing, in the first three-dimensional image and the second three-dimensional image that are each the identified three-dimensional image.

11. The information processing apparatus according to claim 9, wherein a correspondence is established between a predetermined moving amount of the scroll operation and the determined spacing, and the plurality of two-dimensional images included in the first three-dimensional image and the plurality of two-dimensional images included in the second three-dimensional image which are interlocked, are displayed at the display unit, according to the moving amount of the scroll operation.

* * * * *